US00PP09550P

United States Patent [19]

Matsumoto et al.

[11] Patent Number: Plant 9,550

[45] Date of Patent: May 14, 1996

[54] CITRUS TREE 'AMAKUSA'

[75] Inventors: Ryoji Matsumoto; Masashi Yamamoto, both of Nagasaki; Yoshi Yamada, Shimizu; Naomi Okudai, Wakayama; Hidekazu Ikemiya, Okinawa; Kensuke Asada, Omura; Iwao Oiyama, deceased, late of Tokyo, by Kazuko Oiyama, legal representative; Hirono Murata, Onoe; Katsuichi Yoshinaga, Nagasaki; Meisaku Koizumi; Toru Iwanami, both of Shimizu, all of Japan

[73] Assignee: Fruit Tree Research Station, Ministry of Agriculture, Forestry and Fisheries, Tsukuba, Japan

[21] Appl. No.: 404,827

[22] Filed: Mar. 15, 1995

[51] Int. Cl.[6] ..... A01H 5/00

[52] U.S. Cl. ..... Plt./45

[58] Field of Search ..... Plt./45

[56] References Cited

PUBLICATIONS

A New Citrus Cultivar "Amakusa", Jour. Japanese Soc. Hort. Sci. 62, (Suppl. 2), 1993, pp. 29 to 31.

Fruit Tree Seed and Seedling Tangor "Amakusa", 1993, pp. 74 to 75.

*Primary Examiner*—James R. Feyrer

*Attorney, Agent, or Firm*—Armstrong, Westerman, Hattori, McLeland & Naughton

[57] ABSTRACT

Disclosed is a citrus tree having a moderate spreading vigor, and bearing medium size and round shaped fruit with a deep orange skin color and a low acidity. This new and distinct variety of citrus tree is an early maturing citrus cultivar, is fairly resistant to diseases, was bred by a crossing of "T-378" (the seed parent) and "Page" (the pollen parent), bears good quality fruit, and is an excellent citrus cultivar.

3 Drawing Sheets

BACKGROUND OF THE VARIETY

The present invention relates to a new and distinct variety of citrus tree, and more particularly, to a citrus tree maturing early in the season, having a fruit with an easy peeling characteristic, a good appearance and bearing an excellent table fruit.

In Japan, the variety 'Kiyomi', which is a late maturing cultivar, has been cultured, to provide a table fruit, but the fruit of this variety may have an undesirable peeling characteristic, and their flesh is low in (eating) quality. On the contrary, the fruit of the present cultivar has a low acidity level and a moderate sweetness, to provide a good table fruit; the fruit produced by the same has an easy peeling characteristic and a good appearance; and the present variety is an early maturing cultivar.

The breeding by the present breeders has been aimed at obtaining a new variety that can replace 'Kiyomi' Namely, the object of the invention is to provide a new and distinct variety of citrus tree ripening early in the season, having an easy peeling characteristics and a good appearance, and bearing an excellent table fruit.

ORIGIN AND ASEXUAL REPRODUCTION OF THE VARIETY

This new variety of citrus tree was a cross-seedling obtained from a crossing of 'T-378' (♀) (the seed parent) and 'Page' (♂) (the pollen parent) at the Kuchinotsu Branch, Fruit Tree Research Station (Otsu-870, Kuchinotsu-cho, Minamitakaki-gun, Nagasaki-ken, Japan).

Specifically, this crossing was carried out at the Kuchinotsu Branch in 1982, and in 1983 the resulting seeds were sown in a breeding field to grow seedlings. The seedlings obtained were top-worked to a *Citrus unshiu* Marc. for interstock, to shorten juvenile phase, in September, 1983, and the trees thus-grown started bearing in 1987, and were selected based on the good appearance and quality of the fruit of the trees. The trees were given a strain name 'Kuchinotsu 16', and then tests for regional adaptability and of specific character were conducted at several research stations from 1988 to 1993. As a result, it was found that the trees had stable characteristics, and can be distinguished from other similar varieties. The breeders denominated the aforesaid citrus variety of tree in accordance with this invention as 'Amakusa'. The genus of the cultivar is "Citrus", and the group of the same is "tangor".

The aforesaid variety 'T-378' is the seed parent and is a early maturing citrus that always provides a monoembryonic cross seedling, has an easy peeling characteristic, and bears fruit with a soft and juicy flesh and a good taste. Another variety 'Page' is an early maturing citrus and bears fruit that are easily peeled and have a high sweetness and a relatively strong resistance to disease.

The breeders asexually reproduced this new and distinct variety of citrus tree 'Amakusa' by grafting, at the Kuchinotsu Branch, and at other branch of the Fruit Tree Research Station, Ministry of Agriculture, Forestry and Fisheries, Japan, and confirmed the homogeneity and stability of 'Amakusa' according to this invention.

An application for this new variety of citrus tree 'Amakusa' under the Seeds and Seedlings Law of Japan was filed on Mar. 30, 1993, under the filing number 5969.

SUMMARY OF THE VARIETY

This new variety of citrus tree has a moderate vigor with growth habit of slight spreading, and the shoots of the same have an internode with a moderate thickness and length. There are few thorns on the tree, and the shape of the leaf of the tree is fusiform and mainly wavy, similar in appearance to 'Kiyomi'. The size of the leaf is smaller than that of 'Kiyomi', and is larger than that of 'Page'. The flower is solitary, and is of moderate size. The color of the flower is white (JHSC 3702) yellowish white (ISCC-NBC value), and it has 5 petals. The pollen of the flower is fertile. The tree has a parthenocarpic bearing habit. The bearing age and fruit set percentage of the tree are medium.

The fruit generally has a weight of about 200 g, which is bigger than that of 'Page', but is smaller than that of 'Kiyomi'. The shape of the fruit is rounded and squat, wider than it is tall, with the apex being flattened. The skin of the fruit has a reddish orange-color; and is the same color as 'Page'. The optimum color of the fruit is reached in mid-December. The surface of the fruit is smooth and the skin is thin, and is easily peeled, with the peeling characteristic being the same as that of 'Kiyomi' and 'Page'. The flesh is orange-colored. The texture of the flesh is soft and juicy, and has a moderate sweetness, a low acidity, and a low flavor. The segments of the flesh are thin, the content of citric acid in the flesh starts to decrease at a early date, and the rippening time of the fruit appears to be in late December to late February, i.e., it is an early maturing variety. The embryo is pale green (JHSC 2501: pale yellow green (ISCC-NBC value)) colored, and is polyembryoric.

Regarding damage by diseases, the tree of this invention has resistance to scab and canker, and moderate resistance to cold.

The color values presented herein are taken from the Japanese Horticultural Plant Standard Color Chart (JHSC) and the Inter-Society Color Council-National Bureau of Standards (ISCC-NBC).

DESCRIPTION OF THE VARIETY

Figure 1:
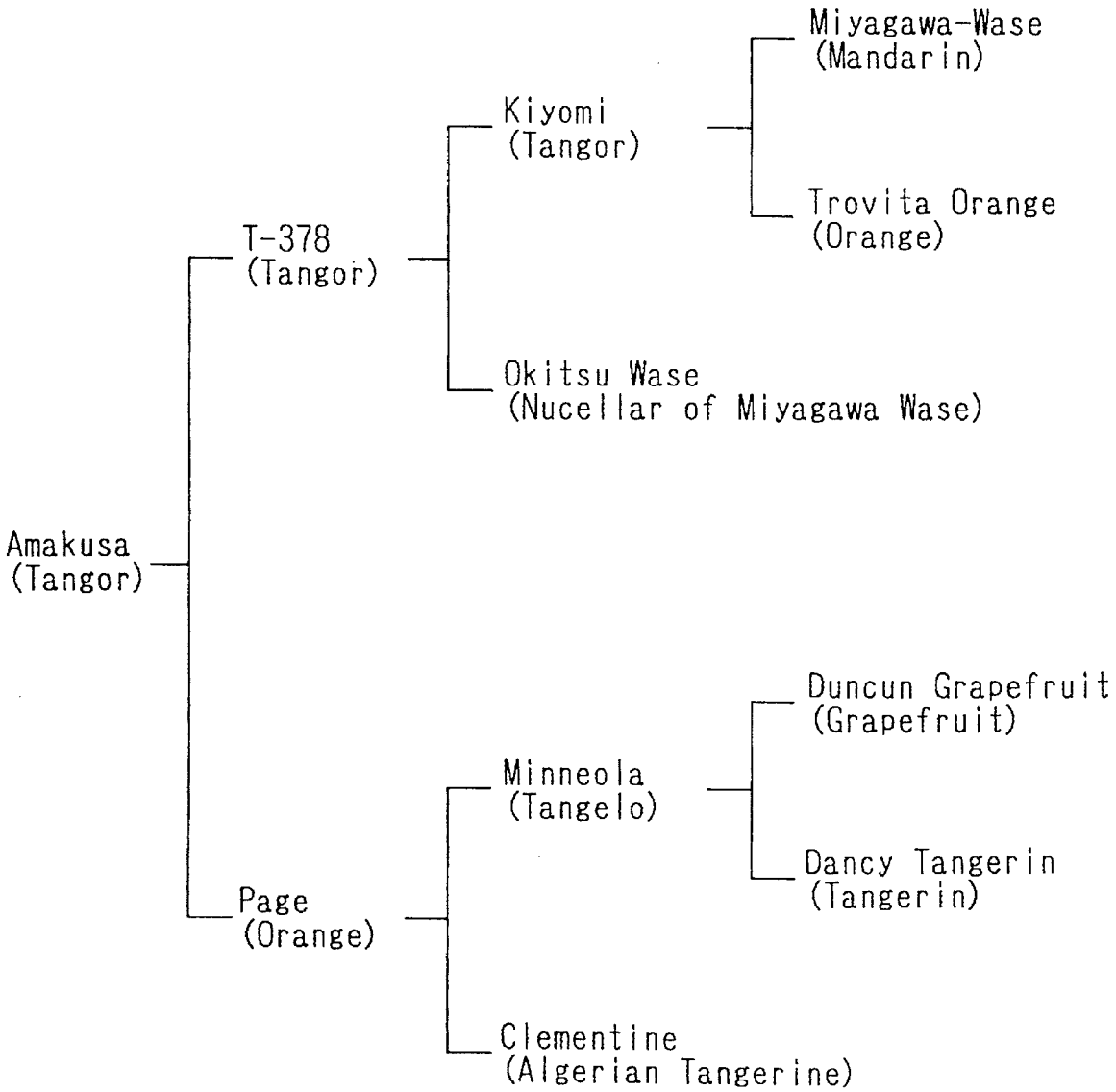
FIG. 1 gives the pedigree of the new and distinct variety of the citrus tree 'Amakusa'.
Figure 2:
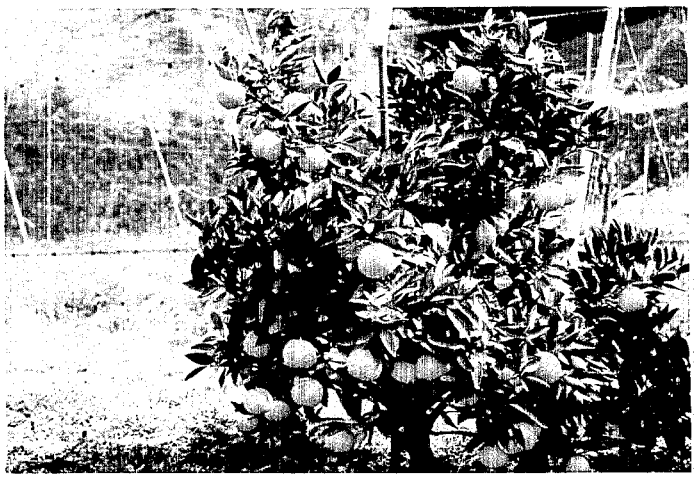
FIG. 2 is a photograph of a shape of the new variety of citrus tree.
Figure 3:
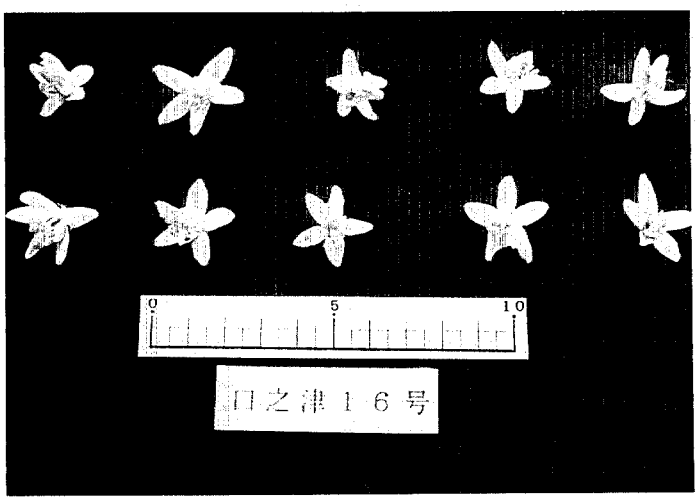
FIG. 3 is a photograph of the flowers of the new variety of citrus tree.
Figure 4:
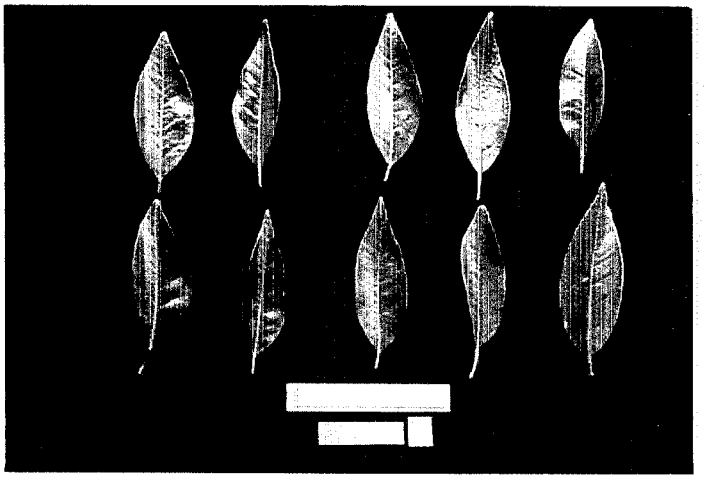
FIG. 4 is a photograph of adult leaves of the new variety of citrus tree.
Figure 5:
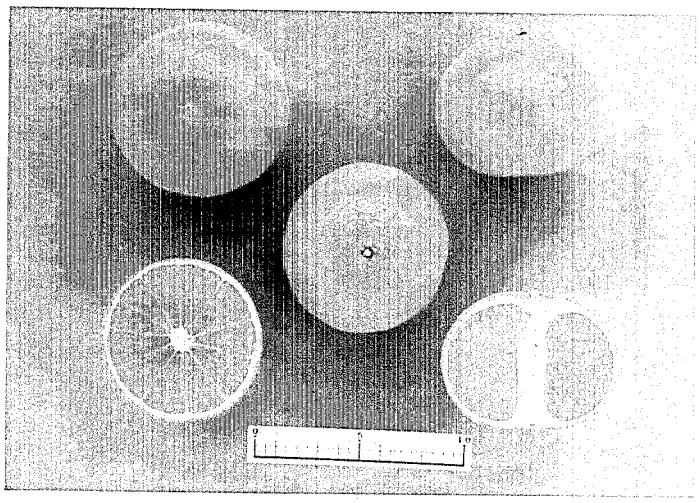
FIG. 5 is a photograph of a stylar end (upper left side), side view (upper right side), basal end (central), cross-sectional view (lower left side) and longitudinal-sectional view (lower right side) of the fruit of the new variety of citrus tree.

The characteristics of the new and distinct variety of citrus tree 'Amakusa' are as follows:

Tree and branch:

*Habit of branches.*—Slightly spreading.
*Size of tree.*—Medium.
*Vigor.*—Medium.
*Thickness of shoot.*—Medium.
*Length of internode.*—Medium.
*Number of prickles on shoot.*—A few. (All of the above characteristics of the variety are similar to those of 'Kiyomi' (K) and 'Page' (P)).

Leaf:

*Leaf blade shape index.*—Medium, 2.29% (K: 2.32%, P: 2.11%).
*Angle of leaf blade apex.*—Sharp, 44.0° (K: 43.0°, P: 42.9°).
*Angle of leaf blade base.*—Moderate, 57.0° (K: 56.5°, P: 59.7°).
*Thickness of leaf blade.*—Thin, 0.42 mm (K: 0.42 mm, P: 0.45 mm).
*Area of leaf blade.*—Small, 31.2 $cm^2$ (K: 30.2 $cm^2$, P: 20.5 $cm^2$).
*Length of leaf blade.*—Short, 10.1 cm (K: 10.1 cm, P: 8.0 cm).
*Width of leaf blade.*—Medium. 4.4 cm (K: 4.3 cm, P: 3.8 cm).
*Sharpness of vein.*—Unclear, same as "K" and "P".
*Shape of wings.*—4.6, (K: none, P: 2.54).
*Length of petiole.*—Medium, 2.0 cm (K: 1.6 cm, P: 1.3 cm).
*Rate of petiole.*—0.13 (K: 0.18).

Flower:

*Formation of inflorescence.*—Single.
*Weight of flower bud.*—Light, 0.41 g.
*Shape of petal apex.*—Sharp.
*Shape of petal base.*—Flat.
*Length of petal.*—Short 12.00 mm (K: 14.00 mm).
*Color of petal.*—White (yellowish white ISCC-NBC).
*Number of petals.*—(K: 5, P: 5).
*Degree of separation of filament.*—Separate, same as "K" and "P".
*Fertility of pollen.*—Fertile.
*Size of ovary.*—Short, 2.5 mm.

Fruit:

*Shape of fruit.*—Round (K: Round, P: Round).
*Shape of fruit stylar end.*—Flat (K: Round, P: Flat).
*Size of stylar scar.*—Small, 0.8 mm.
*Shape of basal end.*—Round.
*Number of radially corrugated fruit on peduncle.*—Very few, 0.2.
*Size of columella in cross-section.*—Small, 3.0% (K: 3.2%).
*Size of fruit.*—Medium, 230 g (K: 328 g, P: 102 g).
*Color of overskin.*—Deep orange (ISCC-NBC Vivid Orange).
*Size of oil glands.*—Large (K: Medium, P: Medium).
*Type of skin surface.*—Smooth, same as "P", K: Medium.
*Density of oil glands.*—Low Density, 42.0 oil glands/$cm^2$ (K: 34.0 g/$cm^2$).
*Irregularity of oil glands.*—Irregular (K: Slightly irregular).
*Number of dents.*—None.
*Thickness of peel.*—Thin, 3.0 mm (K: 4.2 mm, P: 2.2 mm).
*Hardness of peeling.*—Moderate.
*Toughness of segment membrane.*—Medium (K: Soft, P: Soft).
*Shape of juice sac.*—Spindle-shape.
*Size of juice sac.*—Large.
*Color of juice sac.*—Orange (ISCC-NBC Vivid Orange).
*Juice amount.*—Low.
*Sweetness.*—Moderate (Brix 11.0°–12.0°).
*Acidity.*—Low.
*Number of seed.*—Rare.
*Color of embryo.*—Pale Green (ISCC-NBC Pale yellow Green).
*Number of embryo.*—Polyembryony.
*Germination time*.*—Medium, Early April.
*Flowering time*.*—Medium, Early May.
*Time of maturity of fruit*.*—Early (Late December–Early January).
*Alternate bearing.*—Medium.
*Physiological characteristics.*—Occurrence of sunburn: Very little. Occurrence of peel puffing: Very little. Occurrence of fruit cracking: Moderate. Resistance to disease: Relatively Strong. Resistance to pests: Moderate.

*in the Nagasaki prefecture district, Japan

We claim:

1. A new and distinct variety of citrus tree, substantially as illustrated and described herein, characterized over known citrus trees by (A) having a moderate vigor with a growth habit of slightly spreading; (B) having a round type fruit, with a deep orange skin color, and a smooth skin; wherein said fruit is easily peeled; and the flesh of the fruit has a soft texture, a low orange flavor and a low acidity, is juicy and sweet; and thus said fruit is suitable as table fruit; (C) maturing early in the season.

* * * * *

Pedigree of the 'Amakusa' Tangor

UNITED STATES PATENT AND TRADEMARK OFFICE

CERTIFICATE OF CORRECTION

PATENT NO.: Plant 9,550
DATED : May 14, 1996
INVENTOR(S): Matsumoto et al

It is certified that error appears in the above-identified patent and that said Letters Patent is hereby corrected as shown below:

Cover page, Item [75] correct "Yoshi Yamada" to --Yoshio Yamada--.

Signed and Sealed this

Sixteenth Day of June, 1998

*Attest:*

*Attesting Officer*

BRUCE LEHMAN

*Commissioner of Patents and Trademarks*